(12) United States Patent
Kim et al.

(10) Patent No.: US 9,924,869 B2
(45) Date of Patent: Mar. 27, 2018

(54) METHOD AND APPARATUS FOR DETERMINING BLOOD FLOW REQUIRED, METHOD AND APPARATUS FOR PRODUCING BLOOD FLOW IMAGE, AND METHOD AND APPARATUS FOR PROCESSING MYOCARDIAL PERFUSION IMAGE

(71) Applicant: Samsung Electronics Co., Ltd., Suwon-si (KR)

(72) Inventors: Kyung Hwan Kim, Yongin-si (KR); Hyong Euk Lee, Suwon-si (KR); Na Hyup Kang, Seoul (KR); Sang Wook Kim, Seoul (KR); Ji Yeon Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 723 days.

(21) Appl. No.: 13/949,632

(22) Filed: Jul. 24, 2013

(65) Prior Publication Data
US 2014/0029835 A1 Jan. 30, 2014

(30) Foreign Application Priority Data
Jul. 27, 2012 (KR) .................... 10-2012-0082704

(51) Int. Cl.
| | | |
|---|---|---|
| *A61B 5/02* | (2006.01) | |
| *G06F 19/00* | (2018.01) | |
| *A61B 5/00* | (2006.01) | |
| *A61B 6/00* | (2006.01) | |
| *G06T 7/12* | (2017.01) | |
| *G06T 7/149* | (2017.01) | |

(52) U.S. Cl.
CPC ............ *A61B 5/0044* (2013.01); *A61B 6/507* (2013.01); *G06T 7/12* (2017.01); *G06T 7/149* (2017.01); *G06T 2207/30101* (2013.01); *G06T 2207/30104* (2013.01)

(58) Field of Classification Search
None
See application file for complete search history.

(56) References Cited

U.S. PATENT DOCUMENTS

| | | | |
|---|---|---|---|
| 6,352,509 B1 | 3/2002 | Kawagishi et al. | |
| 6,507,753 B1 | 1/2003 | Xue et al. | |
| 9,226,672 B2 * | 1/2016 | Taylor ................ | A61B 5/02007 |
| 2005/0064416 A1 | 3/2005 | Fishman et al. | |
| 2008/0097210 A1 | 4/2008 | Salgo et al. | |
| 2009/0077681 A1 | 3/2009 | Fishman et al. | |
| 2010/0241404 A1 | 9/2010 | Taylor et al. | |
| 2011/0110488 A1 | 5/2011 | Lardo et al. | |
| 2012/0041318 A1 | 2/2012 | Taylor | |
| 2012/0041739 A1 | 2/2012 | Taylor | |
| 2012/0121151 A1 | 5/2012 | Bernhardt et al. | |
| 2012/0122777 A1 | 5/2012 | Daimon et al. | |
| 2014/0247970 A1 † | 9/2014 | Taylor | |

FOREIGN PATENT DOCUMENTS

| | | |
|---|---|---|
| KR | 10-2007-0026319 A | 3/2007 |
| KR | 10-2008-0052662 A | 6/2008 |
| WO | WO 2009/045368 A1 | 4/2009 |

OTHER PUBLICATIONS

Harbinson et al. (Noninvasive Imaging of Myocardial Ischemia (2006); eds. Anagnostopoulos et al., Springer-Verlag, London, pp. 1-15).*
Extended European Search Report dated Oct. 17, 2017 in corresponding European Application No. 13177945.6 (10 pages in English).

\* cited by examiner
† cited by third party

*Primary Examiner* — Lori A. Clow
(74) *Attorney, Agent, or Firm* — NSIP Law

(57) ABSTRACT

A method of determining a required blood flow includes obtaining morphological information of a coronary artery in a cardiac image, segmenting the cardiac image into at least one myocardial region based on the morphological information of the coronary artery, and determining a blood flow required for each of the at least one myocardial region.

20 Claims, 14 Drawing Sheets

METHOD AND APPARATUS FOR DETERMINING BLOOD FLOW REQUIRED, METHOD AND APPARATUS FOR PRODUCING BLOOD FLOW IMAGE, AND METHOD AND APPARATUS FOR PROCESSING MYOCARDIAL PERFUSION IMAGE

CROSS-REFERENCE TO RELATED APPLICATIONS

This application claims the benefit under 35 USC 119(a) of Korean Patent Application No. 10-2012-0082704 filed on Jul. 27, 2012, in the Korean Intellectual Property Office, the disclosure of which is incorporated herein by reference in its entirety for all purposes.

BACKGROUND

1. Field

The following description relates to a method of determining a required blood flow based on a medical image, a method of producing a blood flow image, and a method of processing a myocardial perfusion image.

2. Description of Related Art

Ischemic heart disease (IHD) is a disease characterized by reduced blood supply of the heart muscle, usually due to coronary artery stenosis. Diagnosing IHD may be largely based on detection of an abnormality in a motion of the heart wall, determination of a degree of cardiac stenosis based on a shape of a coronary artery, and quantitative measurement of a blood flow to the myocardium.

To detect an abnormality in a motion of the heart wall, echocardiography (ECG), cardiac cine magnetic resonance imaging (MRI), and other techniques known to one of ordinary skill in the art may be used. To determine a degree of cardiac stenosis based on a shape of a coronary artery, coronary computed tomography (CT) angiography, magnetic resonance (MR) angiography, catheter coronary angiography (CAG), intravascular ultrasound (IVUS), and other techniques known to one of ordinary skill in the art may be used. To measure a blood flow to the myocardium quantitatively, a pressure guide wire, positron emission tomography (PET), single-photon emission computed tomography (SPECT), perfusion MRI, and other techniques known to one of ordinary skill in the art may be used.

Use of image processing techniques in diagnosing of IHD has advanced at a rapid rate. Applications of these image processing techniques in a medical image of the heart or cardiovascular system may achieve an accurate, simple, convenient, and non-invasive diagnosis of IHD.

SUMMARY

In one general aspect, a method of determining a required blood flow includes obtaining morphological information of a coronary artery in a cardiac image; segmenting the cardiac image into at least one myocardial region based on the morphological information of the coronary artery; and determining a blood flow required for each of the at least one myocardial region.

The segmenting of the cardiac image may include segmenting the cardiac image into the at least one myocardial region based on a distance from the coronary artery based on the morphological information of the coronary artery.

The segmenting of the cardiac image may further include determining a plurality of myocardial regions closest to the coronary artery to be one myocardial region.

The determining of the required blood flow may include determining the blood flow required for each of the at least one myocardial region based on a volume of each of the at least one myocardial region.

The determining of the required blood flow may further include calculating a mass of each of the at least one myocardial region based on the volume of each of the at least one myocardial region and an average myocardial density; calculating an oxygen demand for each of the at least one myocardial region based on the calculated mass of each of the at least one myocardial region; and determining the blood flow required for each of the at least one myocardial region based on the calculated oxygen demand for each of the at least one myocardial region.

In another general aspect, a method of generating a blood flow image includes obtaining morphological information of a coronary artery on a heart in a cardiac image of a user; acquiring myocardial blood flow distribution information from a myocardial perfusion image of the heart; and generating a blood flow image of the coronary artery based on the myocardial blood flow distribution information and the morphological information of the coronary artery.

The generating of the blood flow image of the coronary artery may include segmenting the cardiac image into at least one myocardial region based on the morphological information of the coronary artery; determining a blood flow required for each of the at least one myocardial region; adjusting the required blood flow based on the myocardial blood flow distribution information; and generating the blood flow image of the coronary artery based on the adjusted required blood flow and physiological information of the user.

The segmenting of the cardiac image may include segmenting the cardiac image into the at least one myocardial region based on a distance from the coronary artery based on the morphological information of the coronary artery.

The segmenting of the cardiac image may further include determining a plurality of myocardial regions closest to the coronary artery to be one myocardial region.

The determining of the required blood flow may include determining the blood flow required for each of the at least one myocardial region based on a volume of each of the at least one myocardial region.

The determining of the required blood flow may further include calculating a mass of each of the at least one myocardial region based on the volume of each of the at least one myocardial region and an average myocardial density; calculating an oxygen demand for each of the at least one myocardial region based on the calculated mass of each of the at least one myocardial region; and determining the blood flow required for each of the at least one myocardial region based on the calculated oxygen demand for each of the at least one myocardial region.

The adjusting of the required blood flow may include adjusting the required blood flow based on a blood flow distribution curve derived from the myocardial perfusion image.

The generating of the blood flow image of the coronary artery may include generating the blood flow image of the coronary artery by applying the adjusted required blood flow and the physiological information of the user to the morphological information of the coronary artery.

In another general aspect, a method of processing a myocardial perfusion image includes obtaining morphological information of a coronary artery on a heart in a cardiac image of a user; estimating myocardial blood flow distribution information from a myocardial perfusion image of the heart based on the morphological information of the coronary artery; and processing the myocardial perfusion image based on the estimated myocardial blood flow distribution information to improve a precision of the myocardial perfusion image.

The estimating of the myocardial blood flow distribution information may include segmenting the cardiac image into at least one myocardial region based on the morphological information of the coronary artery; determining a blood flow required for each of the at least one myocardial region; and estimating the myocardial blood flow distribution information from the myocardial perfusion image based on the required blood flow and physiological information of the user.

The determining of the required blood flow may include calculating a mass of each of the at least one myocardial region based on a volume of each of the at least one myocardial region and an average myocardial density; calculating an oxygen demand for each of the at least one myocardial region based on the calculated mass of each of the at least one myocardial region; and determining the blood flow required for each of the at least one myocardial region based on the calculated oxygen demand for each of the at least one myocardial region.

The processing of the myocardial perfusion image may include adjusting myocardial blood flow distribution information acquired from the myocardial perfusion image based on the estimated myocardial blood flow distribution information.

In another general aspect, an apparatus for determining a required blood flow includes a coronary artery identifying unit configured to obtain morphological information of a coronary artery in a cardiac image; a myocardial region segmentation unit configured to segment the cardiac image into at least one myocardial region based on the morphological information of the coronary artery; and a required blood flow determining unit configured to determine a blood flow required for each of the at least one myocardial region.

In another general aspect, an apparatus for generating a blood flow image includes a coronary artery identifying unit configured to obtain morphological information of a coronary artery on a heart in a cardiac image of a user; a blood flow distribution information acquisition unit configured to acquire myocardial blood flow distribution information from a myocardial perfusion image of the heart; and a blood flow image generating unit configured to generate a blood flow image of the coronary artery based on the myocardial blood flow distribution information and the morphological information of the coronary artery.

In another general aspect, an apparatus for processing a myocardial perfusion image includes a coronary artery identifying unit configured to obtain morphological information of a coronary artery on a heart in a cardiac image of a user; a blood flow distribution information estimating unit configured to estimate myocardial blood flow distribution information from a myocardial perfusion image of the heart based on the morphological information of the coronary artery; and a myocardial perfusion image processing unit configured to process the myocardial perfusion image based on the estimated myocardial blood flow distribution information to improve a precision of the myocardial perfusion image.

Other features and aspects will be apparent from the following detailed description, the drawings, and the claims.

DETAILED DESCRIPTION

Figure 1:
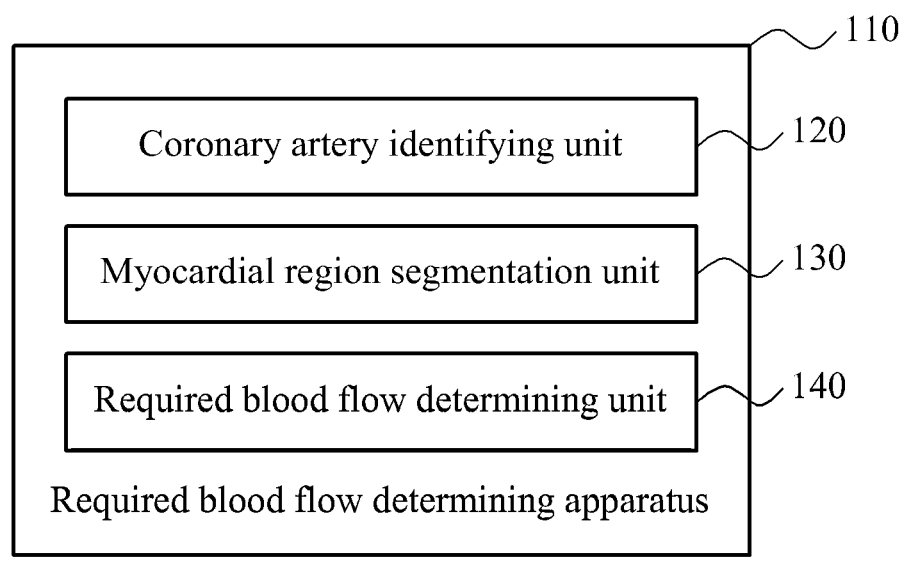
FIG. 1 is a block diagram illustrating an example of a required blood flow determining apparatus.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, description of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

FIG. 1 is a block diagram illustrating an example of a required blood flow determining apparatus 110. The required blood flow determining apparatus 110 may determine a blood flow required for the myocardium based on a cardiac image showing a shape of the heart. The cardiac image may be generated by diagnosis equipment using a medical imaging technique, for example, magnetic resonance imaging (MRI), computed tomography (CT), and other techniques known to one of ordinary skill in the art. In the cardiac image, an internal or external geometric structure of the heart may be represented in a three-dimensional (3D) form through image processing. The required blood flow may refer to a blood flow to be supplied to the myocardium for a normal action of the myocardium.

Referring to FIG. 1, the required blood flow determining apparatus 110 includes a coronary artery identifying unit 120, a myocardial region segmentation unit 130, and a required blood flow determining unit 140. The required blood flow determining apparatus 110 may perform a method of determining a required blood flow described with reference to FIG. 7.

Figure 7:
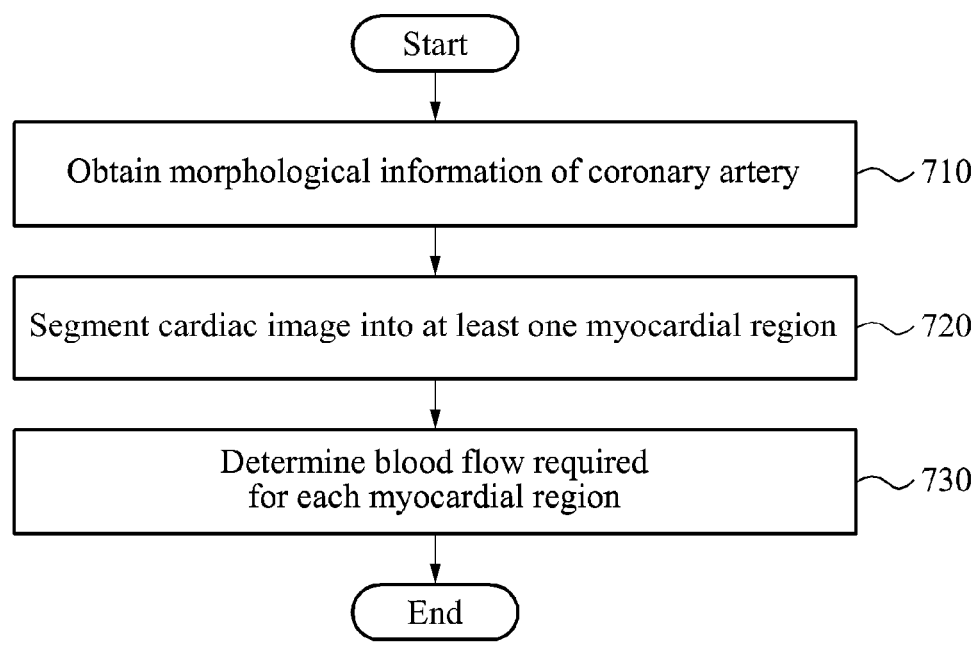
FIG. 7 is a flowchart illustrating an example of a method of determining a required blood flow.

FIG. 7 is a flowchart illustrating an example of a method of determining a required blood flow. Referring to FIG. 7, in 710, the coronary artery identifying unit 120 obtains morphological information of a coronary artery in a cardiac image.

For example, the coronary artery identifying unit 120 may obtain a contour of a coronary artery in a cardiac image using an active contour model or a gradient vector flow (GVF) snake algorithm, and may represent the coronary artery in 3D based on the obtained contour of the coronary artery. The active contour model algorithm may be used to detect an edge using a vector field minimizing a defined energy function.

The coronary artery identifying unit 120 may obtain morphological information of the coronary artery in the cardiac image using angiography and CT. For example, the coronary artery identifying unit 120 may use coronary CT angiography (CCTA) to obtain the morphological information of the coronary artery. The CCTA may correspond to an imaging method using CT based on movement of a contrast medium through a blood vessel over time. The coronary artery identifying unit 120 may identify a myocardial region and a cardiovascular region in an image taken through CCTA.

That is, the coronary artery identifying unit 120 may form a Euclidean distance map (EDM) from 3D vexel data obtained through angiography and CT, may generate a discrete medial surface (DMS) based on the formed EDM, and may obtain the morphological information of the coronary artery from the generated DMS.

Also, the coronary artery identifying unit 120 may obtain the morphological information of the coronary artery in the cardiac image using conventional methods known to one of ordinary skill in the art.

In 720, the myocardial region segmentation unit 130 segments the cardiac image into at least one myocardial region based on the morphological information of the coronary artery obtained by the coronary artery identifying unit 120. The myocardial region segmentation unit 130 may segment the cardiac image into at least one myocardial region based on placement of the coronary artery on the heart.

The myocardial region segmentation unit 130 may segment the cardiac image into at least one myocardial region based on a distance from the coronary artery based on the morphological information of the coronary artery. For example, the myocardial region segmentation unit 130 may determine a plurality of myocardial regions close to the coronary artery to be one myocardial region. Myocardial regions may be assigned to each of a plurality of coronary arteries.

Also, the myocardial region segmentation unit 130 may estimate a portion of the coronary artery supplying a blood flow to each segmented myocardial region. That is, the myocardial region segmentation unit 130 may estimate each portion of the coronary artery supplying a blood flow to the myocardial regions.

Although in this example the myocardial region segmentation unit 130 segments the cardiac image into the myocardial regions based on the morphological information of the coronary artery, the myocardial region segmentation unit 130 may perform segmentation using various schemes known to one of ordinary skill in the art.

For example, although in this example the myocardial region segmentation unit 130 performs segmentation based on a distance from the coronary artery, the myocardial region segmentation unit 130 may perform segmentation based on a cross-sectional area of the coronary artery. As the cross-sectional area of the coronary artery becomes greater, the myocardial region segmentation unit 130 may provide a higher weight value.

In 730, the required blood flow determining unit 140 determines a blood flow required for each myocardial region segmented by the myocardial region segmentation unit 130. For example, the required blood flow determining unit 140 may determine a blood flow required for each segmented myocardial region based on a volume of each myocardial region.

Figure 8:
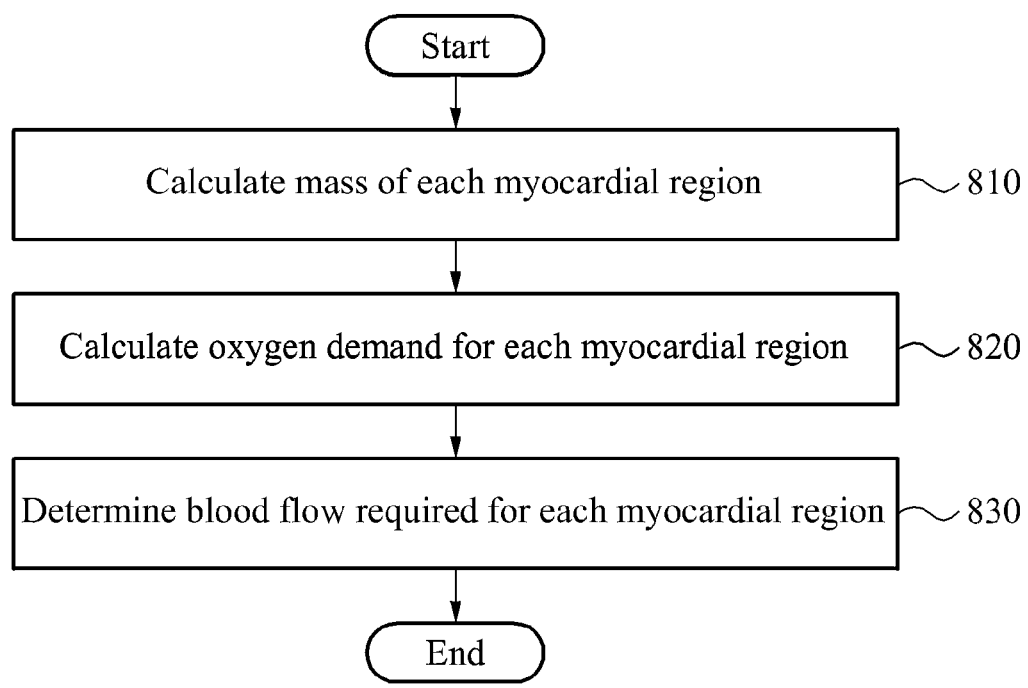
FIG. 8 is a flowchart illustrating an example of a method of determining a required blood flow for each myocardial region.

The required blood flow determining unit 140 may determine the blood flow required for each segmented myocardial region based on the volume of each myocardial region using a method of FIG. 8.

FIG. 8 is a flowchart illustrating an example of a method of determining a blood flow required for each myocardial region. Referring to FIG. 8, in 810, the required blood flow determining unit 140 calculates a mass of each myocardial region based on a volume of each myocardial region and an average myocardial density.

The required blood flow determining unit 140 may measure the volume of each myocardial region based on a number of volume pixels, also known as voxels, in the cardiac image taken through CT. The required blood flow determining unit 140 may measure the mass of each myocardial region based on the measured volume of each myocardial region and a clinically measured average myocardial density. For example, the required blood flow determining unit 140 may calculate the mass of each myocardial region by multiplying the volume of each myocardial region by the average myocardial density. This example is not limited to measuring the volume of each myocardial region, and the required blood flow determining unit 140 may measure the volume of each myocardial region using various schemes known to one of ordinary skill in the art.

In 820, the required blood flow determining unit 140 calculates an oxygen demand for each myocardial region based on the calculated mass of each myocardial region.

The required blood flow determining unit 140 may calculate an oxygen demand for each myocardial region based on the mass of each myocardial region and a clinically measured oxygen demand per mass. For example, the required blood flow determining unit 140 may calculate the oxygen demand for each myocardial region by multiplying the mass of each myocardial region by the oxygen demand per mass. The oxygen demand per mass may refer to an amount of oxygen per mass required for a normal action of the myocardium.

In 830, the required blood flow determining unit 140 determines a blood flow required for each myocardial region based on the calculated oxygen demand of each myocardial region.

The required blood flow determining unit 140 may determine the blood flow required for each myocardial region based on the calculated oxygen demand of each myocardial region and a blood flow required based on the clinically measured oxygen demand. The blood flow required based on the oxygen demand may refer to an amount of blood flow to be supplied to human body tissues to meet the oxygen demand.

As the average myocardial density, the oxygen demand per mass, and the blood flow required based on the oxygen demand, a clinically measured average value or an arbitrarily set value may be used.

Figure 2:
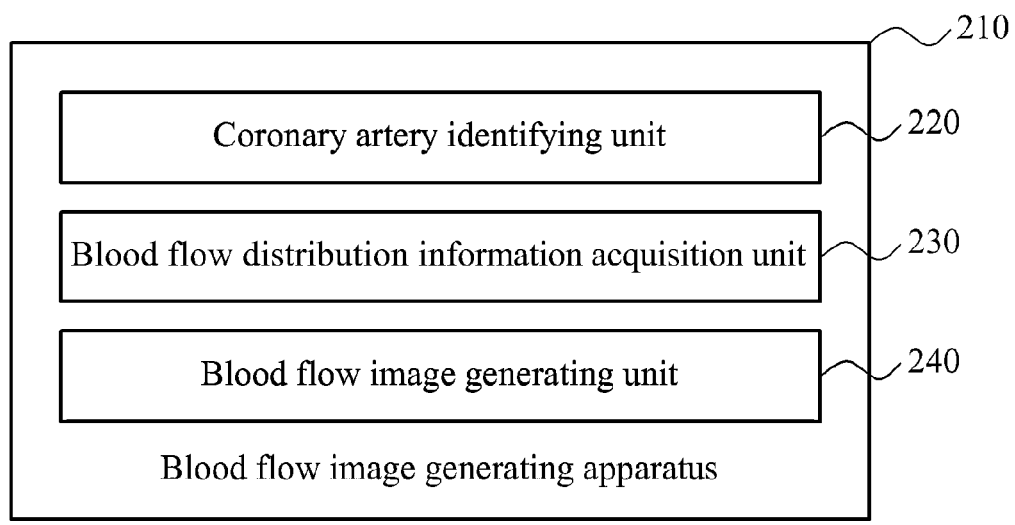
FIG. 2 is a block diagram illustrating an example of a blood flow image generating apparatus.

FIG. 2 is a block diagram illustrating an example of a blood flow image generating apparatus 210. The blood flow image generating apparatus 210 may generate an image of a blood flow in a coronary artery based on morphological information of the coronary artery, blood flow distribution information of the myocardium, and physiological information of a user.

Referring to FIG. 2, the blood flow image generating apparatus 210 includes a coronary artery identifying unit 220, a blood flow distribution information acquisition unit 230, and a blood flow image generating unit 240. The blood flow image generating apparatus 210 may perform a method of generating a blood flow image described with reference to FIG. 9.

Figure 9:
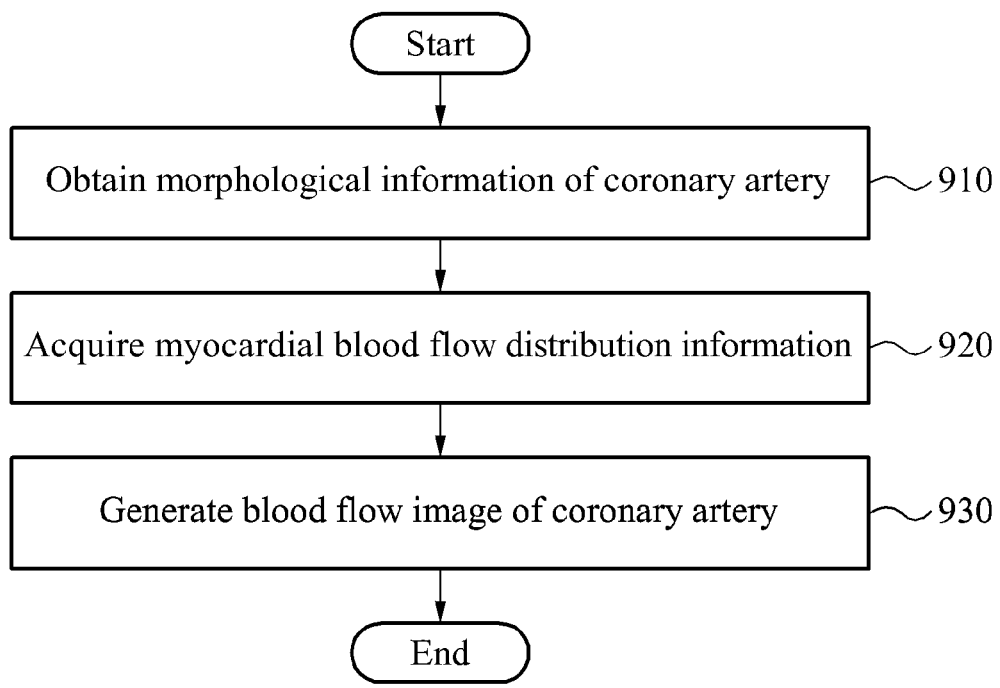
FIG. 9 is a flowchart illustrating an example of a method of generating a blood flow image.

FIG. 9 is a flowchart illustrating an example of a method of generating a blood flow image. Referring to FIG. 9, in 910, the coronary artery identifying unit 220 obtains morphological information of a coronary artery on a heart in a cardiac image. The coronary artery identifying unit 220 may obtain the morphological information of the coronary artery using the method of FIG. 7. For a detailed description, reference may be made to 710 of FIG. 7.

In 920, the blood flow distribution information acquisition unit 230 acquires myocardial blood flow distribution information from a myocardial perfusion image of the heart.

The myocardial perfusion image may correspond to an image of a blood flow in the myocardium, and may be generated by a nuclear medicine test. For example, the myocardial perfusion image may be generated by positron emission tomography (PET) that visualizes the distribution of a positron-emitting radioactive substance in the myocardium after injection into a blood vessel. Also, the myocardial perfusion image may be generated by single-photon emission computed tomography (SPECT) or perfusion MRI using a contrast medium and an MRI scan.

The nuclear medicine test may involve recording radiation emitted from a radioactive substance injected into the body. In the nuclear medicine test, a blood flow distribution in the myocardium may be obtained based on the fact that a radioactive substance is less absorbed in a part of the myocardium to which an insufficient flow of blood is supplied. The blood flow distribution information acquisition unit 230 may acquire information about the blood flow distribution in the myocardium from the myocardial perfusion image generated by the nuclear medicine test.

In 930, the blood flow image generating unit 240 generates a blood flow image of the coronary artery based on the myocardial blood flow distribution information acquired by the blood flow distribution information acquisition unit 230 and the morphological information of the coronary artery. The blood flow image generating unit 240 may perform a method of generating a blood flow image of the coronary artery described with reference to FIG. 10.

Figure 10:
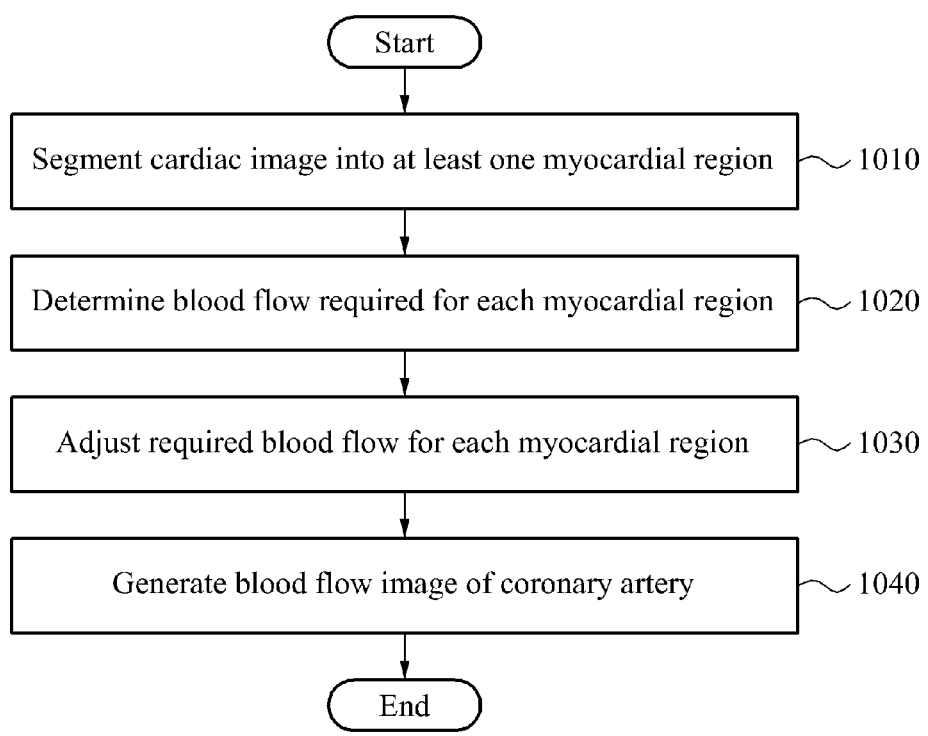
FIG. 10 is a flowchart illustrating an example of a method of generating a blood flow image based on a required blood flow.

FIG. 10 is a flowchart illustrating an example of a method of generating a blood flow image based on a required blood flow. Referring to FIG. 10, in 1010, the blood flow image generating unit 240 segments a cardiac image into at least one myocardial region based on obtained morphological information of a coronary artery.

The blood flow image generating unit 240 may segment the cardiac image into at least one myocardial region based on a distance from the coronary artery based on the morphological information of the coronary artery. For example, the blood flow image generating unit 240 may determine a plurality of myocardial regions close to each portion of the coronary artery to be one myocardial region, and may segment the cardiac image into at least one myocardial region.

Although in this example the blood flow image generating unit 240 segments the cardiac image into the myocardial regions based on the morphological information of the coronary artery, the example is not limited thereto. The blood flow image generating unit 240 may perform segmentation using various schemes known to one of ordinary skill in the art.

In 1020, the blood flow image generating unit 240 determines a blood flow required for each segmented myocardial region. The blood flow image generating unit 240 may determine a blood flow required for each segmented myocardial region based on a volume of each myocardial region. The blood flow image generating unit 240 may determine the blood flow required for each myocardial region using the method of FIG. 8.

For example, the blood flow image generating unit 240 may calculate a mass of each myocardial region based on a volume of the myocardial region and an average myocardial density, may calculate an oxygen demand for each myocardial region based on the calculated mass of each myocardial region, and may determine a blood flow required for each myocardial region based on the calculated oxygen demand for each myocardial region. For a detailed description, reference may be made to FIG. 8.

The required blood flow determined in 1020 may correspond to an estimated blood flow required for a normal action of the myocardium, rather than a blood flow actually measured in the myocardial region.

In 1030, the blood flow image generating unit 240 adjusts the required blood flow determined in 1020 based on the myocardial blood flow distribution information acquired in 920 of FIG. 9.

For example, the blood flow image generating unit 240 may adjust the determined required blood flow based on a blood flow distribution curve derived from the myocardial perfusion image. The blood flow image generating unit 240 may compare the derived myocardial blood flow distribution information with the required blood flow, and when a difference between the determined required blood flow and a myocardial blood flow included in the derived blood flow distribution information exceeds a predetermined threshold range, may adjust the determined blood flow required for each myocardial region by increasing or decreasing a value of the determined required blood flow based on the myocardial blood flow distribution information.

In 1040, the blood flow image generating unit 240 generates a blood flow image of the coronary artery based on the required blood flow adjusted in 1030 and physiological information of a user. The blood flow image generating unit 240 may generate the blood flow image of the coronary artery by applying the adjusted required blood flow and the physiological information of the user to the morphological information of the coronary artery. The blood flow image generating unit 240 may estimate a blood flow to be supplied to each myocardial region based on the adjusted required blood flow.

The physiological information of the user may include a blood pressure, a blood flow rate, a heart rate, a stroke volume, a cardiac output, blood characteristics, a hematocrit (HCT), and other physiological information.

The blood flow image generating unit 240 may generate a blood flow image of the coronary artery using a blood flow model of Equation 1 below.

$$\frac{Du}{Dt} = \frac{\partial u}{\partial t} + (u \cdot \nabla)u = grad\left(\frac{p}{\rho}\right) + v\Delta u + b \qquad (1)$$

In Equation 1, t denotes a period of time, u denotes a blood flow rate, and p denotes a pressure of a blood flow. Also, b denotes interaction modeling between blood cells, v denotes blood viscosity modeling, and ρ denotes blood density modeling. As the interaction modeling, the blood viscosity modeling, and the blood density modeling, an average value used in a corresponding technical field may be available.

The blood flow image generating unit 240 may generate the blood flow image of the coronary artery by applying the physiological information of the user and the adjusted required blood flow to Equation 1. The blood flow image generating unit 240 may generate the blood flow image of the coronary artery by applying a blood flow rate and a blood flow pressure derived from Equation 1 to the morphological information of the coronary artery obtained in 910 of FIG. 9. For example, the blood flow image generating unit 240 may generate the blood flow image of the coronary artery based on the derived blood flow rate and blood pressure, and the blood flow image may contain information regarding a coronary flow reserve (CFR) or a fractional flow reserve (FFR). The FFR may correspond to an index of functional severity of a coronary artery stenosis.

Although in this example the blood flow image generating unit 240 generates the blood flow image of the coronary artery using the blood flow model of Equation 1, the example is not limited in this regard. The blood flow image generating unit 240 may generate the blood flow image of the coronary artery using various blood flow models known to one of ordinary skill in the art.

The blood flow image generating unit 240 may generate the blood flow image with a high precision in which physiological properties of the user are reflected by applying physiological information of the user to the blood flow image. Also, the blood flow image generating unit 240 may generate the blood flow image on which physiological properties of the heart are reflected by employing the required blood flow.

Figure 3:
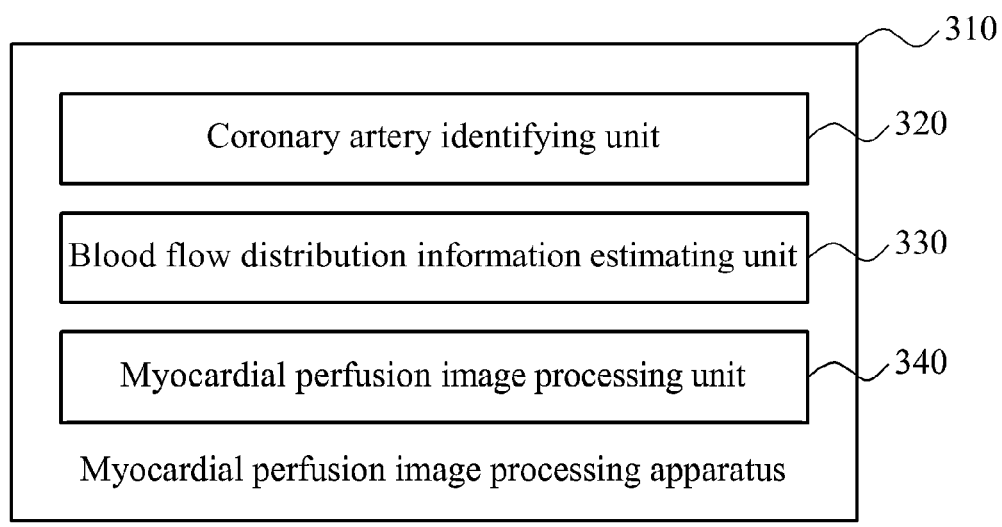
FIG. 3 is a block diagram illustrating an example of a myocardial perfusion image processing apparatus.

FIG. 3 is a block diagram illustrating an example of a myocardial perfusion image processing apparatus 310. The myocardial perfusion image processing apparatus 310 may improve precision of a myocardial perfusion image by applying estimated myocardial blood flow distribution information to the myocardial perfusion image.

Referring to FIG. 3, the myocardial perfusion image processing apparatus 310 includes a coronary artery identifying unit 320, a blood flow distribution information estimating unit 330, and a myocardial perfusion image processing unit 340. The myocardial perfusion image processing apparatus 310 may perform a method of processing a myocardial perfusion image described with reference to FIG. 11.

Figure 11:
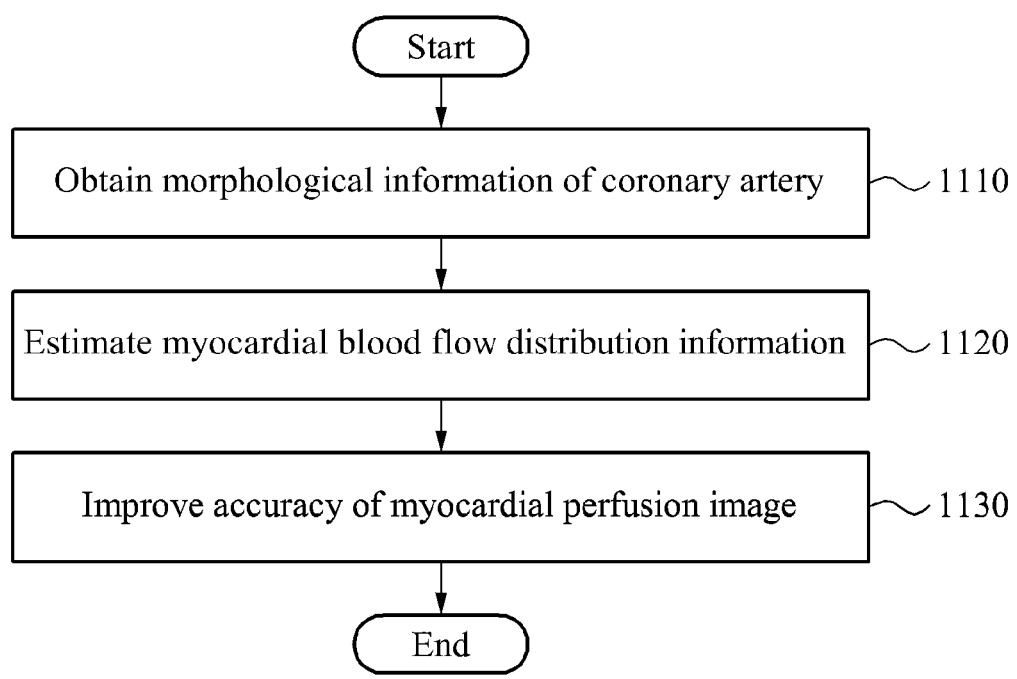
FIG. 11 is a flowchart illustrating an example of a method of processing a myocardial perfusion image.

FIG. 11 is a flowchart illustrating an example of a method of processing a myocardial perfusion image. Referring to FIG. 11, in 1110, the coronary artery identifying unit 320 obtains morphological information of a coronary artery on a heart in a cardiac image. The coronary artery identifying unit 320 may obtain the morphological information of the coronary artery using the method of FIG. 7. For a detailed description, reference may be made to 710 of FIG. 7.

In 1120, the blood flow distribution information estimating unit 330 estimates myocardial blood flow distribution information from the morphological information of the coronary artery obtained by the coronary artery identifying unit 320. The blood flow distribution information estimating unit 330 may estimate the myocardial blood flow distribution information using a method of estimating myocardial blood flow distribution information described with reference to FIG. 12.

Figure 12:
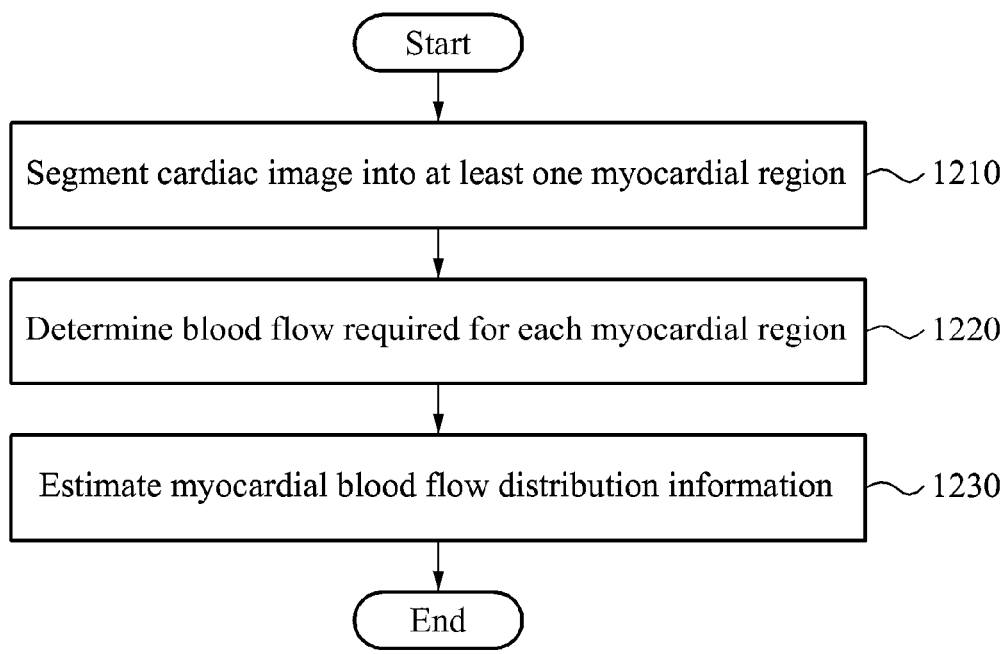
FIG. 12 is a flowchart illustrating an example of a method of estimating blood flow distribution information.

FIG. 12 is a flowchart illustrating an example of a method of estimating blood flow distribution information. Referring to FIG. 12, in 1210, the blood flow distribution information estimating unit 330 segments a cardiac image into at least one myocardial region based on the obtained morphological information of the coronary artery. The blood flow distribution information estimating unit 330 may segment the cardiac image into the myocardial regions using the method of FIG. 7. For a detailed description, reference may be made to 720 of FIG. 7.

In 1220, the blood flow distribution information estimating unit 330 determines a blood flow required for each segmented myocardial region. The blood flow distribution information estimating unit 330 may determine the blood flow required for each myocardial region using the method of FIG. 8. For a detailed description, reference may be made to FIG. 8.

For example, the blood flow distribution information estimating unit 330 may calculate a mass of each myocardial region based on a volume of each myocardial region and an average myocardial density, calculate an oxygen demand for each myocardial region based on the calculated mass of each myocardial region, and determine a blood flow required for each myocardial region based on the calculated oxygen demand for each myocardial region. For a detailed description, reference may be made to FIG. 8.

In 1230, the blood flow distribution information estimating unit 330 estimates myocardial blood flow distribution information based on the required blood flow determined in 1220 and physiological information of the user.

For example, the blood flow distribution information estimating unit 330 may estimate the myocardial blood flow distribution information using the blood flow model of Equation 1 used in 1040 of FIG. 10. That is, the blood flow distribution information estimating unit 330 may estimate the myocardial blood flow distribution information by applying, to the blood flow model, the required blood flow determined in 1220 and the physiological information of the user, for example, a blood flow rate, a blood pressure, a hematocrit, and other physiological information.

The estimated blood flow distribution information may correspond to information estimated through modeling, rather than actually measured information. However, each of pixels representing the shape of the myocardium may include blood flow distribution information through modeling.

Referring to FIG. 11 once again, in 1130, the myocardial perfusion image processing unit 340 may improve a precision of the myocardial perfusion image based on the blood flow distribution information estimated by the blood flow distribution information estimating unit 330.

The myocardial perfusion image processing unit 340 may adjust the blood flow distribution information acquired from the myocardial perfusion image based on the blood flow distribution information estimated by the blood flow distribution information estimating unit 330.

For example, the myocardial perfusion image processing unit 340 may compare the estimated blood flow distribution information with the myocardial blood flow distribution information acquired from the myocardial perfusion image actually taken. In this case, the myocardial perfusion image processing unit 340 may use a blood flow distribution curve derived from the myocardial perfusion image. According to the result of the comparison, the myocardial perfusion image processing unit 340 may adjust the blood flow distribution information acquired from the myocardial perfusion image by increasing or decreasing a value of the myocardial blood flow distribution information based on the estimated blood flow distribution information.

According to another example, the myocardial perfusion image processing unit 340 may adjust the blood flow distribution information in the myocardial perfusion image by interpolating a pixel value of a pixel including the estimated blood flow distribution information and a pixel value of a pixel including the myocardial blood flow distribution information in the myocardial perfusion image.

The myocardial perfusion image processing unit 340 may generate the myocardial perfusion image with an improved precision by adjusting the blood flow distribution information in the myocardial perfusion image based on the blood flow distribution information estimated through modeling.

Figure 4A:
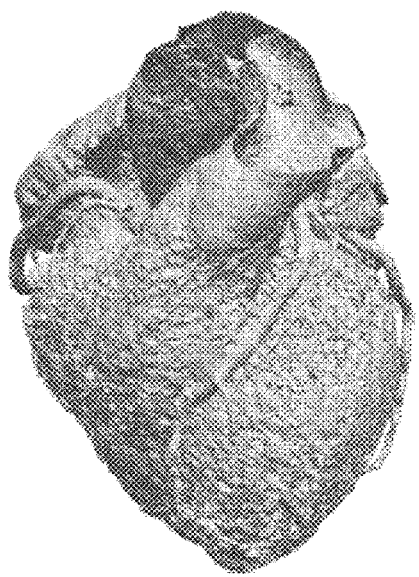
FIGS. 4A through 4C are diagrams illustrating an example of segmentation of a cardiac image into myocardial regions.
Figure 4B:
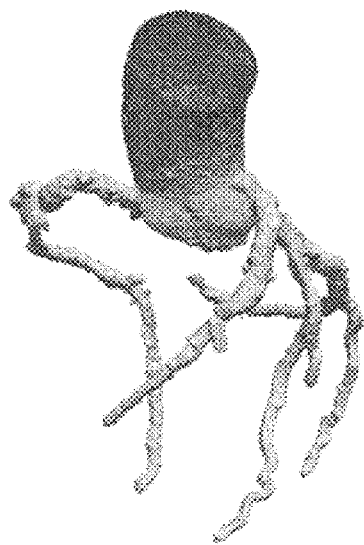
Figure 4C:
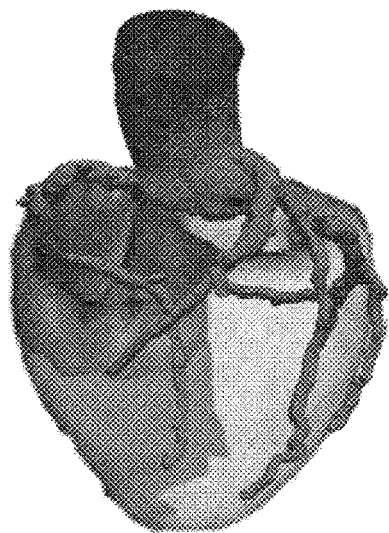

FIGS. 4A through 4C are diagrams illustrating an example of segmentation of a cardiac image into myocardial regions. FIG. 4A is a diagram illustrating a cardiac image of a heart of a user, FIG. 4B is a diagram illustrating a coronary artery identified in the cardiac image, including morphological information of the coronary artery on the heart, and FIG. 4C is a diagram illustrating segmented myocardial regions based on the morphological information of the coronary artery.

Referring to FIG. 4A, the cardiac image may be generated by diagnosis equipment based on a medical imaging technique, for example, MRI, CT, and other medical imaging techniques known to one of ordinary skill in the art.

Referring to FIG. 4B, the required blood flow determining apparatus may obtain morphological information including a contour of the coronary artery in the cardiac image. The required blood flow determining apparatus may use an active contour model or a GVF snake algorithm to obtain the morphological information of the coronary artery as described in 710 of FIG. 7.

Referring to FIG. 4C, the required blood flow determining apparatus may segment the cardiac image into at least one myocardial region based on the obtained morphological information of the coronary artery. For example, the required blood flow determining apparatus may segment the cardiac image into the myocardial regions based on a distance from the coronary artery.

Although the description of FIG. 4C states that the required blood flow determining apparatus segments the cardiac image into the myocardial regions, the blood flow image generating apparatus and the myocardial perfusion image processing apparatus may also perform segmentation.

Figure 5:
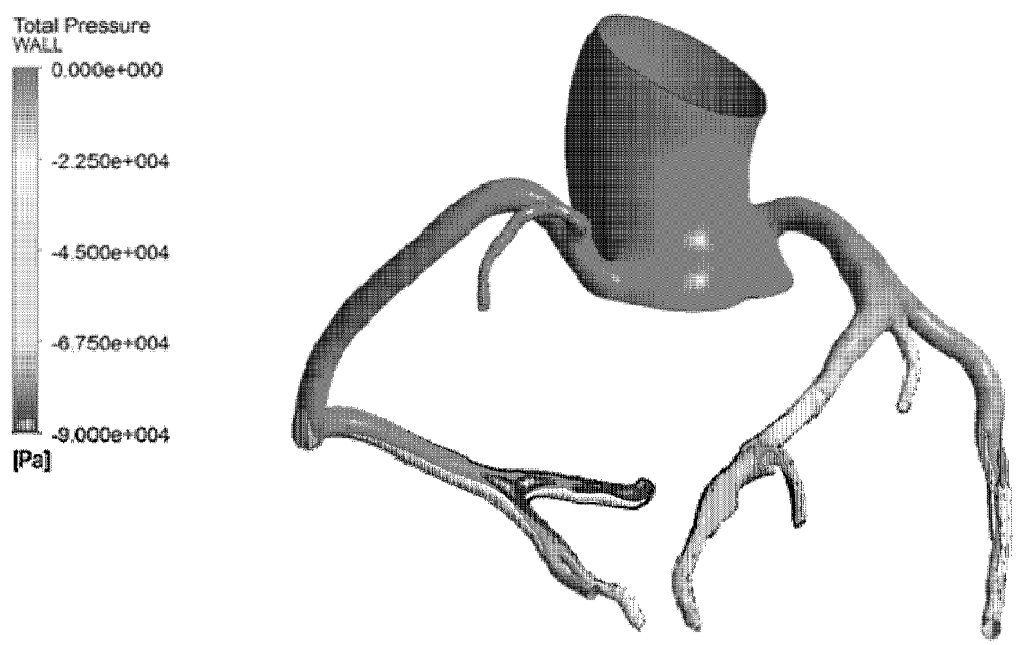
FIG. 5 is a diagram illustrating an example of a blood flow image generated by a blood flow image generating apparatus.

FIG. 5 is a diagram illustrating an example of a blood flow image generated by a blood flow image generating apparatus. The blood flow image generating apparatus may generate a blood flow image of a coronary artery based on a required blood flow determined for each myocardial region and myocardial blood flow distribution information. The required blood flow determined for each myocardial region may correspond to an estimated blood flow required for each myocardial region. The blood flow image generating apparatus may acquire myocardial blood flow distribution information from an actually taken myocardial perfusion image. The blood flow image generating apparatus may generate a blood flow image of FIG. 5 by adjusting the required blood flow determined for each myocardial region based on the myocardial blood flow distribution information.

Referring to FIG. 5, the morphological information of the coronary artery may include an FFR. The blood flow image generating apparatus may simulate a blood flow of the coronary artery based on the required blood flow and the myocardial blood flow distribution information. The blood flow image generating apparatus may generate a high-precision blood flow image based on the required blood flow derived based on actual blood flow distribution information and the morphological information of the coronary artery.

Figure 6A:
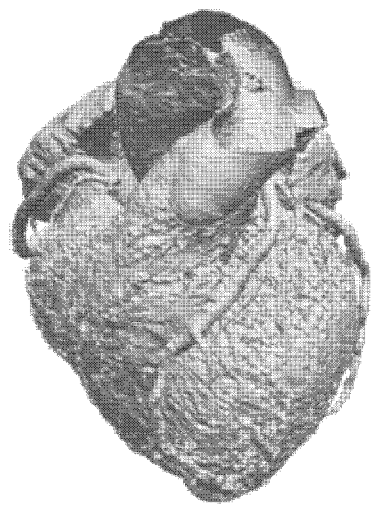
FIGS. 6A through 6C are diagrams illustrating an example of a method of processing a myocardial perfusion image.
Figure 6B:
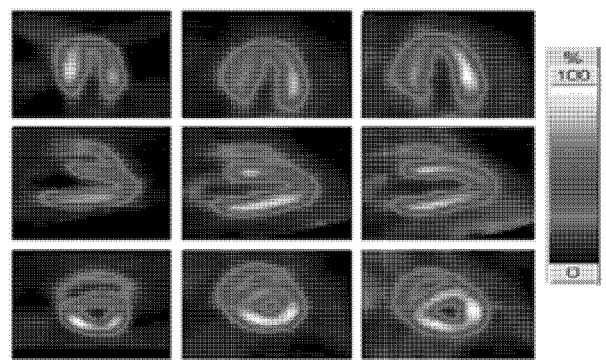
Figure 6C:
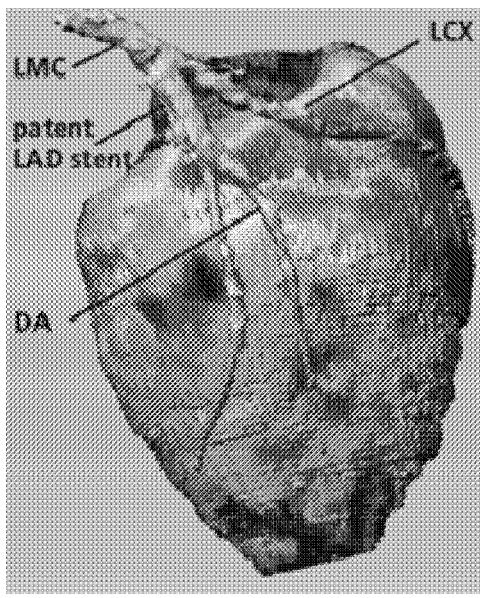

FIGS. 6A through 6C are diagrams illustrating an example of a method of processing a myocardial perfusion image. FIG. 6A is a diagram illustrating a cardiac image, FIG. 6B is a diagram illustrating a myocardial perfusion image taken actually through PET, and FIG. 6C is a diagram illustrating a myocardial perfusion image with an improved precision.

Referring to FIG. 6A, the myocardial perfusion image processing apparatus may obtain morphological information of a coronary artery in a cardiac image, and may estimate myocardial blood flow distribution information by applying the obtained morphological information of the coronary artery and physiological information of a user to a blood flow model. The estimated myocardial blood flow distribution information may correspond to information estimated through modeling.

Referring to FIG. 6B, the myocardial perfusion image processing apparatus may improve a precision of the myocardial perfusion image based on the estimated myocardial blood flow distribution information. For example, the myocardial perfusion image processing apparatus may improve a precision of the myocardial perfusion image by adjusting blood flow distribution information in an actually taken myocardial perfusion image based on the estimated myocardial blood flow distribution information or by interpolating pixel values of the image.

Referring to FIG. 6C, the myocardial perfusion image processing apparatus may display the myocardial perfusion image through post-processing. It may be found that the myocardial blood flow distribution is depicted with an improved precision.

The required blood flow determining apparatus 110, the coronary artery identifying unit 120, the myocardial region segmentation unit 130, the required blood flow determining unit 140, the blood flow image generating apparatus 210, the coronary artery identifying unit 220, the blood flow distribution information acquisition unit 230, the blood flow image generating unit 240, the myocardial perfusion image processing apparatus 310, the coronary artery identifying unit 320, the blood flow distribution information estimating unit 330, and the myocardial perfusion image processing unit 340 described above that perform the operations illustrated in FIGS. 4A-4C, 5, 6A-6C, and 7-12 may be implemented using one or more hardware components, one or more software components, or a combination of one or more hardware components and one or more software components.

A hardware component may be, for example, a physical device that physically performs one or more operations, but is not limited thereto. Examples of hardware components include resistors, capacitors, inductors, power supplies, frequency generators, operational amplifiers, power amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:
1. A method of determining a required blood flow, the method comprising:
obtaining morphological information of a coronary artery in a cardiac image of a user;

segmenting the cardiac image into a plurality of myocardial regions based on the morphological information of the coronary artery;

calculating a mass of each of the plurality of segmented myocardial regions based on an average myocardial density;

determining a myocardial blood flow required for normal myocardial action for each of the plurality of segmented myocardial regions based on the calculated mass of each of the plurality of segmented myocardial regions;

adjusting the myocardial blood flow required for normal myocardial action for each of the plurality of segmented myocardial regions based on blood flow distribution information derived from a myocardial perfusion image of the user; and generating a blood flow image of the coronary artery by applying the adjusted myocardial blood flow required for normal myocardial action for each of the plurality of segmented myocardial regions and physiological information of the user to the morphological information of the coronary artery of the user.

2. The method of claim 1, wherein the segmenting of the cardiac image comprises segmenting the cardiac image into the plurality of segmented myocardial regions based on a distance from the coronary artery based on the morphological information of the coronary artery.

3. The method of claim 2, wherein the segmenting of the cardiac image further comprises determining a plurality of myocardial regions closest to the coronary artery to be one myocardial region.

4. The method of claim 1, wherein the calculating of the mass of each of the plurality of segmented myocardial regions comprises calculating the mass of each of the plurality of segmented myocardial regions based on the average myocardial density and a volume of each of the plurality of segmented myocardial regions.

5. The method of claim 1, wherein the determining of the myocardial blood flow required for normal myocardial action for each of the plurality of segmented myocardial regions comprises:

calculating an oxygen demand required for normal myocardial action for each of the plurality of segmented myocardial regions based on the calculated mass of each of the plurality of segmented myocardial regions; and determining the myocardial blood flow required for normal myocardial action for each of the plurality of segmented myocardial regions based on the calculated oxygen demand required for normal myocardial action for each of the plurality of segmented myocardial regions.

6. A method of generating a blood flow image, the method comprising:

obtaining morphological information of a coronary artery on a heart in a cardiac image of a user;

estimating myocardial blood flow distribution information from the morphological information of the coronary artery based on a myocardial blood flow required for normal myocardial action determined based on an oxygen demand required for normal myocardial action;

acquiring measured myocardial blood flow distribution information from a myocardial perfusion image of the heart;

adjusting the estimated myocardial blood flow distribution information based on the measured myocardial blood flow distribution information; and generating a blood flow image of the coronary artery by applying the adjusted myocardial blood flow distribution information to the morphological information of the coronary artery.

7. The method of claim 6, wherein the estimating of the myocardial blood flow distribution information comprises:

segmenting the cardiac image into a plurality of myocardial regions based on the morphological information of the coronary artery; and determining a myocardial blood flow required for normal myocardial action for each of the plurality of segmented myocardial regions based on an oxygen demand required for normal myocardial action for each of the plurality of segmented myocardial regions; and estimating the myocardial blood flow distribution information based on the myocardial blood flow required for normal myocardial action for each of the plurality of segmented myocardial regions.

8. The method of claim 7, wherein the segmenting of the cardiac image comprises segmenting the cardiac image into the plurality of segmented myocardial regions based on a distance from the coronary artery based on the morphological information of the coronary artery.

9. The method of claim 8, wherein the segmenting of the cardiac image further comprises determining a plurality of myocardial regions closest to the coronary artery to be one myocardial region.

10. The method of claim 7, wherein the determining of the myocardial blood flow required for normal myocardial action for each of the plurality of segmented myocardial regions comprises determining the myocardial blood flow required for normal myocardial action for each of the plurality of segmented myocardial regions based on a volume of each of the plurality of segmented myocardial regions, an average myocardial density, and an oxygen demand per mass required for normal myocardial action.

11. The method of claim 10, wherein the determining of the myocardial blood flow required for normal myocardial action for each of the plurality of segmented myocardial regions further comprises:

calculating a mass of each of the plurality of segmented myocardial regions based on the volume of each of the plurality of segmented myocardial regions and the average myocardial density;

calculating the oxygen demand required for normal myocardial action for each of the plurality of segmented myocardial regions based on the calculated mass of each of the plurality of segmented myocardial regions and the oxygen demand per mass required for normal myocardial action; and determining the myocardial blood flow required for normal myocardial action for each of the plurality of segmented myocardial regions based on the calculated oxygen demand required for normal myocardial action for each of the plurality of segmented myocardial regions.

12. The method of claim 7, wherein the generating of the blood flow image of the coronary artery comprises generating the blood flow image of the coronary artery by applying the adjusted myocardial blood flow distribution information and physiological information of the user to the morphological information of the coronary artery.

13. The method of claim 6, wherein the adjusting of the estimated myocardial blood flow distribution information comprises adjusting the estimated myocardial blood flow distribution information based on a blood flow distribution curve derived from the myocardial perfusion image.

14. A method of processing a myocardial perfusion image, the method comprising:
- obtaining morphological information of a coronary artery on a heart in a cardiac image of a user;
- estimating myocardial blood flow distribution information from the morphological information of the coronary artery;
- comparing the estimated myocardial blood flow distribution information with measured myocardial blood flow distribution information acquired from a myocardial perfusion image;
- adjusting the measured myocardial blood flow distribution information acquired from the myocardial perfusion image based on a result of the comparing; and
- generating a myocardial perfusion image having an improved precision by processing the myocardial perfusion image based on the adjusted myocardial blood flow distribution information.

15. The method of claim 14, wherein the estimating of the myocardial blood flow distribution information comprises:
- segmenting the cardiac image into a plurality of myocardial regions based on the morphological information of the coronary artery;
- determining a myocardial blood flow required for normal myocardial action for each of the plurality of segmented myocardial regions; and
- estimating the myocardial blood flow distribution information based on the myocardial blood flow required for normal myocardial action for each of the plurality of segmented regions and physiological information of the user.

16. The method of claim 15, wherein the determining of the myocardial blood flow required for normal myocardial action for each of the plurality of segmented regions comprises:
- calculating a mass of each of the plurality of segmented myocardial regions based on a volume of each of the plurality of segmented myocardial regions and an average myocardial density;
- calculating an oxygen demand required for normal myocardial action for each of the plurality of segmented myocardial regions based on the calculated mass of each of the plurality of segmented myocardial regions; and
- determining the myocardial blood flow required for normal myocardial action for each of the plurality of segmented myocardial regions based on the calculated oxygen demand required for normal myocardial action for each of the plurality of segmented myocardial regions.

17. The method of claim 14, wherein the processing of the myocardial perfusion image comprises adjusting the myocardial perfusion image based on the adjusted myocardial blood flow distribution information.

18. An apparatus for determining a required blood flow, the apparatus comprising:
- one or more processors configured to:
  - obtain morphological information of a coronary artery in a cardiac image of a user;
  - segment the cardiac image into a plurality of myocardial regions based on the morphological information of the coronary artery;
  - calculate a mass of each of the plurality of segmented myocardial regions based on an average myocardial density;
  - determine a myocardial blood flow required for normal myocardial action for each of the plurality of segmented myocardial regions based on the calculated mass of each of the plurality of segmented myocardial regions;
  - adjust the myocardial blood flow required for normal myocardial action for each of the plurality of segmented myocardial regions based on blood flow distribution information derived from a myocardial perfusion image of the user; and
  - generate a blood flow image of the coronary artery by applying the adjusted myocardial blood flow required for normal myocardial action for each of the plurality of segmented myocardial regions and physiological information of the user to the morphological information of the coronary artery of the user.

19. An apparatus for generating a blood flow image, the apparatus comprising:
- one or more processors configured to:
  - obtain morphological information of a coronary artery on a heart in a cardiac image of a user;
  - estimate myocardial blood flow distribution information from the morphological information of the coronary artery based on a myocardial blood flow required for normal myocardial action determined based on an oxygen demand required for normal myocardial action;
  - acquire measured myocardial blood flow distribution information from a myocardial perfusion image of the heart;
  - adjust the estimated myocardial blood flow distribution information based on the measured myocardial blood flow distribution information; and
  - generate a blood flow image of the coronary artery by applying the adjusted myocardial blood flow distribution information to the morphological information of the coronary artery.

20. An apparatus for processing a myocardial perfusion image, the apparatus comprising:
- one or more processors configured to:
  - obtain morphological information of a coronary artery on a heart in a cardiac image of a user;
  - estimate myocardial blood flow distribution information based on the morphological information of the coronary artery;
  - compare the estimated myocardial blood flow distribution information with measured myocardial blood flow distribution information acquired from a myocardial perfusion image;
  - adjust the measured myocardial blood flow distribution information acquired from the myocardial perfusion image based on a result of the comparing; and
  - generate a myocardial perfusion image having an improved precision by processing the myocardial perfusion image based on the adjusted myocardial blood flow distribution information.

* * * * *